United States Patent [19]
Gunz et al.

[11] Patent Number: 5,880,793
[45] Date of Patent: Mar. 9, 1999

[54] GLARE PROTECTION DEVICE

[75] Inventors: Stefan Gunz, Wadenswil; René Werthmüeller, Ipsach; Livio Ghisleni, Wilen, all of Switzerland

[73] Assignee: Xelux AG, Wadenswil, Switzerland

[21] Appl. No.: 909,104

[22] Filed: Aug. 12, 1997

Related U.S. Application Data

[63] Continuation of Ser. No. 431,531, May 1, 1995, abandoned, which is a continuation-in-part of Ser. No. 90,543, Jul. 13, 1993, abandoned.

[30] Foreign Application Priority Data

Jul. 13, 1992 [CH] Switzerland ................. 02196/92

[51] Int. Cl.⁶ .................... G02F 1/133; A61F 9/06; B23K 9/02
[52] U.S. Cl. ................ 349/14; 219/147; 250/206
[58] Field of Search .................. 359/53, 63, 85, 359/72, 601; 219/132, 147; 2/8, 432; 250/201.1, 206, 214 AL, 214 B; 351/44; 349/13, 14, 116

[56] References Cited

U.S. PATENT DOCUMENTS

| Re. 29,684 | 6/1978 | Gordon | 219/147 |
|---|---|---|---|
| 4,071,912 | 2/1978 | Budminger | 359/66 |
| 4,114,366 | 9/1978 | Renner et al. | 58/50 R |
| 4,152,846 | 5/1979 | Witt | 359/54 |
| 4,241,286 | 12/1980 | Gordon | 349/14 |
| 4,638,146 | 1/1987 | Koyama | 219/147 |
| 4,728,173 | 3/1988 | Toth | 359/53 |
| 5,248,880 | 9/1993 | Fergason | 250/205 |
| 5,252,817 | 10/1993 | Fergason et al. | 250/205 |
| 5,315,099 | 5/1994 | Gunz et al. | 359/63 |

FOREIGN PATENT DOCUMENTS

| 0027518 | 4/1981 | European Pat. Off. . |
|---|---|---|
| 0335056 | 10/1989 | European Pat. Off. . |
| 0349665 | 1/1990 | European Pat. Off. . |
| 3536678 | 7/1986 | Germany . |

OTHER PUBLICATIONS

European Search Report issued Oct. 19, 1993 for EP 93 11 0693.

*Primary Examiner*—William L. Sikes
*Assistant Examiner*—Tai V. Duong
*Attorney, Agent, or Firm*—Blank Rome Comisky & McCauley LLP

[57] ABSTRACT

Electro-optical glare protection device is disclosed for use with protective glasses, protective helmets or protective masks with at least one optical detector, especially a photodiode, with an electro-optical glare protection plate incorporating at least one liquid crystal cell, and with an electronic circuit for the adjustment and setting of the optical transmission of this glare protection plate. The protective device comprises a non-optical detector and a switch connected to the electronic circuit for adjusting the optical transmission of the glare protection plate. The switch links the signals produced by these detectors with each other as an and/or circuit. The electronic circuit generates corresponding switch signals.

9 Claims, 1 Drawing Sheet

GLARE PROTECTION DEVICE

This is a continuation of application Ser. No. 08/431,531, filed on May 1, 1995, now abandoned, which is a CIP of application of Ser. No. 08/090,543, filed on July 13, 1993 and now abandoned.

BACKGROUND OF THE INVENTION

The present invention relates to a glare protection device.

Glare protection devices of this type have long been known to the expert in the art. These devices encompass essentially a filter arrangement with at least one liquid crystal cell, at least one polarizer and one analyzer, as well as various passive light filters, especially IR- and UV-reflective filters. The liquid crystal cell is actuated by an optical-electrical transducer serving as feed current source, and the operating signal for the liquid crystal cell is regulated either manually or from an optical sensor, especially this optical-electrical transducer. The purpose of these filter arrangements is to attain as unvarying as possible an illumination intensity for the eye, while the illumination of the object is exposed to considerable fluctuations.

These and similar filter arrangements have great drawbacks in practical use. In practice it is especially desirable to control the quality of the welding flame, i.e. its light and color. A device which tends to do that, to balance variations of intensity in general, does not allow control of corresponding quality features of the welding flame, and especially the experienced welder gauges from the intensity of the welding flame the appropriate suitable temperature and/or the constancy of the flame arc length for the operation.

Other drawbacks of known devices exist in that light disturbance, e.g. the flickering of lamps or any optional intensity differences in the surrounding light, is likewise picked up and compensated by suitable dimming of the light shield. Thereby the gauging of the flame quality is considerably hampered if not made altogether impossible.

Other sources of interference or malfunction are to be seen in all of the devices which produce non-optical, electrical, magnetic or electromagnetic alternating fields in the wave length range of detectable visible light, as these fields too may be emitted from halogen- or fluorescent-tubes. In particular, high current- and voltage-producing welding machines as used for welding prove to be notable sources of interference.

Another problem with the use of the known filter arrangements exists in that these arrangements are dimmed only when variation of intensity is detected as it occurs during high frequency welding.

However, it is precisely the goal of the manufacturer of modern welding apparatus to be able to produce as quiet as possible and increasingly smaller welding flames. Thus, traditional filter arrangements are no longer suitable in an overall sense to fulfill legally prescribed glare protection regulations.

With the foregoing and other objects, advantages and features of the invention that will become hereinafter apparent, the nature of the invention may be more clearly understood by reference to the following detailed description of the invention, the appended claims and to the several views illustrated in the drawings.

OBJECTS AND SUMMARY OF THE INVENTION

Therefore, it is the object of the present invention to provide a glare protection device which can be used without any problem and as a reliable device for all operations and under all operating conditions, i.e. for any type of welding, which does not have the drawbacks of the known device. Another object of the present invention is to provide a special universal glare protection device which does not react to electromagnetic interference fields and also can be used with quiet and less intensive welding flame light.

These and other objects are attained according to the invention by a glare protection device which links at least optical and electromagnetic sensors in suitable combinations logically and/or cyclically or sequentially with each other.

In addition to the optical sensor, a detector is especially provided, working as an antenna for non-optical signals. The signals from the optical sensor and the non-optical detector are combined in a suitable manner, and the corresponding signals are linked logically with each other in order to switch-connect the liquid crystal cell. By suitable preselection according to use and corresponding programming of a logic circuit, for instance a microprocessor, a number of logic links can be formed.

In particular, the detector signals can be transmitted and processed equally well on wire and/or wireless, as with fiber optics.

BRIEF DESCRIPTION OF THE DRAWING

The exemplary embodiments are to be explained in greater detail hereinafter relative to the two drawings in which.

DETAILED DESCRIPTION OF THE PREFERRED EMBODIMENT

Figure 1:
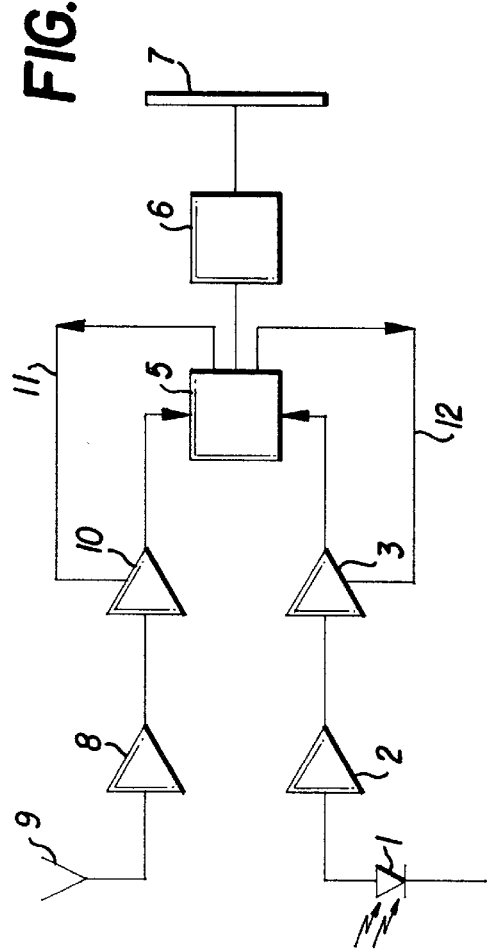
FIG. 1 is a block diagram of an electronic circuit suitable for a glare protection device according to the invention.

Referring now to the FIG. 1 schematic, the signal produced from a photodetector 1 is reinforced by an amplification circuit 2 and digitized and fed to a threshhold value switch 3. The signal produced from this threshhold switch 3 is fed to a switch circuit 5 according to the invention, which essentially activates an LCD-actuator 6, to which is connected a liquid crystal cell 7. According to the invention, this electronic circuit has at least one more detector circuit 9, especially an antenna for electromagnetic alternating fields, the signal of which is fed through an amplification circuit 8 and a threshold switch 10 to the aforementioned circuit 5.

Circuit 5 can process the detected signals in the desired manner, especially in a manually selectable manner, and can be electrically controlled or can work with preprogrammed microprocessors. Circuit 5 is especially intended to be able also to process the incoming detector or sensor signals in cyclically controlled succession, for example, in order to vary the sensitivity of the glare protection device (as is desired, for example, following the intensive start-up spark during welding) or in order to be able to select between optical and non-optical detection. The expert in the art finds it obvious to feed back the signals of circuit 5 through separate lines 11, 12.

Overall, it is conceivable to use other detectors, such as are already known today in many variations in sensor technology. In the present device, heat detectors could also be used, so as to analyze temperature fluctuations, or ultra-sound or microwave fields.

This universality allows the relevant detectors to be positioned independent of each other, and/or also to be configured so that they can be positioned individually by the user.

Figure 2:
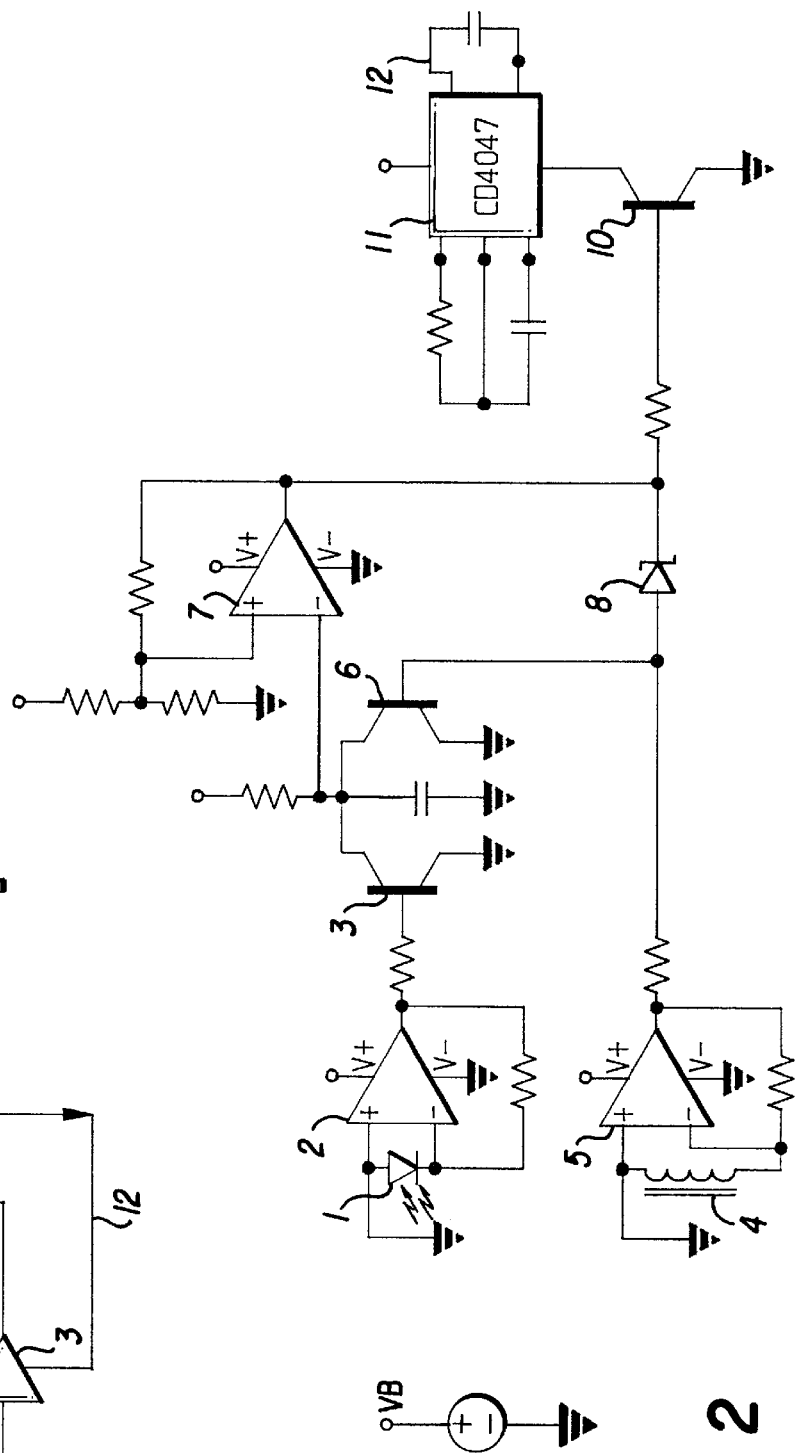
FIG. 2 is a schematic diagram of the circuit of FIG. 1.

Referring to the more detailed schematic of FIG. 2, without any signals from the sensors 1 and 9, the output voltages of the amplifiers 2 and 8 are constantly lower than the switching threshold of the connected transistors 3 and 10. This turns off transistors 3 and 10, and the output signal at their joined collectors rests at the battery voltage level. Thus, negative input to comparator 5 is above the reference voltage at the positive input of comparator 5. This means that the output signal of comparator 5 is at ground level (GND).

The electrical potential of the cathode of the Shottky diode 11 is, therefore, kept low. According to the present invention, this has the effect that any signal which could reach the amplifier 8 via the magnetic sensor 9 is also always lower than the threshold voltage of the switching transistor 10. The magnetic sensor is, therefore, logically switched off into a "Standby" mode.

When the opto-sensor 1 delivers a signal which, after amplification in amplifier 2, is sufficiently strong to switch on transistor 3, the negative input to the comparator 5 drops and, accordingly, the output of the comparator 5 rises to the battery voltage level (VB), thereby blocking the Shottky diode 11. Only then can possible magnetic signals switch on the transistor 10, via the pickup antenna 9 and the amplifier 8, and the comparator 5 remains switched on even though no opto-signals of sufficient amplitude are received any longer. This circuitry implements a so-called "magnetic hold feature".

The capacitor 5a provides for the necessary switch-off delay. The comparator 5, via the switching transistor 6a, supplies the oscillator 6b with operating voltage, so that the connected LCD screen 7 darkens.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An electro-optical glare protection device for at least one of protective glasses, protective helmets and protective masks, comprising:

a glare protection plate having varying optical transmission characteristics;

circuit means connected to said glare protection plate for applying an operating voltage thereto for varying the optical transmission level of said glare protection plate;

optical detector means for detecting light adjacent to said glare protection plate and providing a first input signal to said circuit means; and non-optical detector means for detecting a non-optical condition adjacent to said glare protection plate and providing a second input signal to said circuit means;

wherein said circuit means selectively enables and disables optical transmission by said glare protection plate in response to said first and second input signals; and wherein said circuit means comprises a first threshold switch for receiving said first input signal and a second threshold switch for receiving said second input signal, and a comparator means having an additional input for comparing a reference voltage input to said additional input, said additional input being connected in common to respective outputs of said first and second threshold switches.

2. The device of claim 1, wherein said circuit means further comprises an actuator, wherein said comparator means supplies said operating voltage to said actuator, and wherein said actuator applies said operating voltage to said glare protection plate.

3. The device of claim 1, wherein said comparator means responds to a first condition of said additional input by enabling optical transmission by said glare protection plate and responds to a second condition of said additional input by disabling optical transmission by said glare protection plate.

4. The device of claim 1, further comprising blocking means connected between an output of said comparator means and an output of said non-optical detector means for blocking said second input signal in response to detection of a given input condition by said comparator means.

5. The device of claim 4, wherein said blocking means comprises a Shottky diode.

6. The device of claim 1, wherein said comparator means responds to a given condition of said additional input by enabling optical transmission by said glare protection plate, said circuit means further comprising delay means for delaying disabling of optical transmission by said glare protection plate for a period of time after said given condition of said additional input no longer exists.

7. The device of claim 6, wherein said delay means comprises a capacitor connected in common to said first and second threshold switches and to said additional input of said comparator means.

8. The device of claim 1, wherein said non-optical detector means comprises an electromagnetic field detector.

9. The device of claim 1, wherein said non-optical detector means comprises a wireless detector.

\* \* \* \* \*